United States Patent [19]

Barker

[11] Patent Number: 5,360,824

[45] Date of Patent: Nov. 1, 1994

[54] HUMAN SKIN CLEANSING AND WRINKLE-REDUCING CREAM

[76] Inventor: Donald E. Barker, 28931 S. Lake Shore Dr., Agoura, Calif. 91301

[21] Appl. No.: 15,966

[22] Filed: Feb. 5, 1993

[51] Int. Cl.$^5$ .................. A61K 7/44; A61K 7/48; A61K 9/06

[52] U.S. Cl. .................. 424/680; 424/60; 514/969; 514/846; 514/474; 514/251; 514/276; 514/249; 252/129

[58] Field of Search .............. 424/59, 60; 514/844, 514/846

[56] References Cited

U.S. PATENT DOCUMENTS

| | | | |
|---|---|---|---|
| 3,092,111 | 6/1963 | Saperstein | 128/355 |
| 3,487,916 | 1/1970 | Moroni | 206/047 |
| 3,607,161 | 9/1971 | Monick | 51/307 |
| 3,910,284 | 10/1975 | Orentreich | 128/355 |
| 3,944,506 | 3/1976 | Hramchenko | 252/545 |
| 4,048,123 | 9/1977 | Hramchenko | 252/545 |
| 4,172,552 | 12/1987 | Panghurn | 128/355 |
| 4,751,075 | 6/1988 | Chernowsky et al. | 514/904 |
| 4,769,022 | 9/1988 | Chang | 604/368 |
| 4,786,432 | 11/1988 | Kaufer | 252/120 |
| 4,818,521 | 4/1989 | Tamabuelu | 514/938 |
| 4,957,747 | 9/1990 | Stiefel | 424/691 |
| 4,990,339 | 2/1991 | Scholl | 424/443 |
| 5,089,269 | 2/1992 | Noda et al. | 424/401 |
| 5,198,225 | 3/1993 | Meybeck et al. | 424/401 |
| 5,208,028 | 5/1993 | Clement et al. | 424/401 |

*Primary Examiner*—Dale R. Ore
*Attorney, Agent, or Firm*—John J. Posta, Jr.

[57] ABSTRACT

The improved cleansing cream has a wrinkle-reducing effect when periodically applied to and rubbed into the human skin in wrinkled skin areas. The cream is non-irritating to the skin and includes a plurality of water-soluble granules which are of sufficient size, quantity and hardness to abrade the keratinized outer epidermal layer of the skin. The granules may be one or more inorganic salt, but preferably include one or more water-soluble vitamins and/or water-soluble vitamin-yielding salts, The cream also includes a base in which the granules are substantially uniformly disposed. The base preferably is in a major proportion with respect to the granules and is an oil and a petrolatum jelly. The water-soluble granules do not clog the pores of the skin but are absorbed into and nourish the skin.

9 Claims, No Drawings

HUMAN SKIN CLEANSING AND WRINKLE-REDUCING CREAM

BACKGROUND OF THE INVENTION

1. Field of the Invention

The present invention generally relates to beauty aids and more particularly to an improved type of human skin cleansing cream which reduces wrinkles and does not irritate the skin or clog the skin pores.

2. Prior Art

A wide variety of human skin cleansing and wrinkle-reducing creams have been provided to the public. Most of such creams are devoted to prevention of wrinkling of the skin by keeping it moist. Wrinkling occurs as moisture and skin oils are removed from the skin under conditions of low humidity and due to the drying action of the sun and wind.

However, certain of such creams are formulated to abrade the keratinized outer layer of epidermis when used according to directions. The object with those creams is to strip off the wrinkled outer layer of epidermis and thus permit unwrinkled new layers of epidermis to form and/or be exposed to view. Typically, the skin-abrading creams utilize water-insoluble particles of inorganic oxides such as alumina, silica and the like. Irritation of the skin frequently occurs as a result of the frictional action of the abrading particles. Moreover, when the particle size of the abrasize particles is sufficiently small to reduce skin irritation, clogging of the skin pores with the particles can occur. This can result in skin rashes, inflammations, infections, and cysts, besides reducing the general tone and quality of the skin.

Typical of the patented skin-abrading formulations are those set forth in U.S. Pat. No. 3,092,111. Those formulations utilize water-insoluble abrading particles in a non-oleaginous base. U.S. Pat. Nos. 3,944,506 and 4,048,123 disclose similar formulations. U.S. Pat. Nos. 3,487,916, 3,910,284, 4,712,552, and 4,769,022 disclose the use of various abrasive pads which are used to rub off the keratinized skin in an attempt to improve its texture. Such means are subject to the skin-clogging and skin-irritating effects previously described.

Accordingly, it would be desirable to provide an improved means of cleansing the skin and reducing skin wrinkles without irritating the skin or clogging its pores. Preferably, such formulations should be easy to apply, soothing and capable of embodying skin-nourishing ingredients in a spreadable cream.

SUMMARY OF THE INVENTION

All of the above objects are achieved through the improved skin-cleansing and wrinkle-reducing cream of the present invention. The cream is substantially as set forth in the Abstract of the Disclosure.

Thus, the formulation of the present invention employs an oleaginous base and for that reason is termed herein a cream. The base has substantially uniformly distributed therein a plurality of water-soluble, skin-abrading granules or particles which are of a material which does not irritate the skin. Preferably, the base is an edible oil and/or petrolatum jelly. The granules preferably comprise inorganic non-irritating salt such as sodium chloride. Most preferably, the salt is of a vitamin. Preferred examples of vitamin-yielding salts comprise calcium pantothenate, calcium ascorbate, calcium citrate and sodium p-aminobenzoate, although other such salts of the vitamins can also be used. The granules can also be of compacted, crystalline, water-soluble vitamins, such as ascorbic acid (Vitamin C), folic acid (a B-complex vitamin) or the like.

The granules are of any suitable size distribution, e.g., about 100 microns to about 1 millimeter, which provides a gentle skin-abrading effect. Even very small particle sizes which could otherwise clog the skin can be used. But since the particles are water-soluble, clogging does not occur, the natural moisture of the skin dissolving them in situ. Moreover, where the granules are vitamin-yielding salts, the moisture of the skin converts the salts to the vitamins and provides clog-free deep nourishment to the skin for improved skin texture, tone and health. When the particles are water-soluble vitamins, the same effect is obtained. All these factors promote the growth of wrinkle-free epidermal layers while still performing the desired skin-cleansing action.

The soluble particles cause exfoliation of the skin without causing silicones as can occur with sand or similar products.

Further features of the present invention are set forth in the following detailed description.

DETAILED DESCRIPTION

The improved skin cleansing and wrinkle-reducing human skin-treating formulation of the present invention is for the purposes of the present disclosure referred to as a cream. That term is used in the usual cosmetic sense. In this regard, the base for the cream is an oleaginous substance. That substance can be an oil. While anyoil which is non-irritating to the skin can be used, it is preferred to use inexpensive and perfectly suitable edible oil, most preferably vegetable oil such as sunflower seed oil, peanut oil, corn oil, canola oil or the like.

In place of the oil or in addition thereto, the oleaginous substance can include petrolatum jelly, such as that sold under the registered trademark vaseline by Chesebrough-Ponds, Inc. VASELINE is a mixture of hydrocarbons having a melting point between 38° and 60° and is non-irritating to the skin, often being used as an ointment for skin burns and the like. Petrolatum jelly has the advantage of thickening the present formulation so that the cream has the skin-gripping aspect of an ointment, while still providing necessary lubricity so that the formulation can be easily rubbed around on the skin.

While normally in the cream formulation of the present invention the base comprises a major proportion by weight of the formulation, other proportions of ingredients are possible. In the formulation, water-soluble, skin-abrading, wrinkle-reducing and skin-cleansing granules or particles are normally present in a minor proportion by weight of the formulation. The skin-abrading granules are water-soluble so that they cannot clog the skin pores, but instead can be dissolved and absorbed by the skin.

The skin-abrading granules can be in any suitable size range from, for example, about 100 microns average diameter to as large as several millimeters or more. The granules are non-irritating to the skin and may comprise inorganic salt particles, for example, sodium carbonate, sodium bicarbonate or the like.

Alternatively, or in addition to the inorganic salt, the particles may comprise water-soluble organic salt, preferably of one or more vitamins. In this regard, calcium pantothenate, calcium ascorbate and sodium para-amino benzoate, among others, can be used. When such particles contact the skin, they gradually dissolve to yield, respectively, pantothenic acid, ascorbic acid and para-amino benzoic acid, all of which are skin-nourishing water-soluble vitamins. It will be understood that other water-soluble salts which yield vitamins can be used in the formulation.

Water-soluble crystalline vitamins can be compacted into the desired granules. For example, ascorbic acid (Vitamin C), folic acid (a B-complex Vitamin), and other similar vitamins can be used. Thiamine hydrochloride which yields the B-complex vitamin can also be used. Riboflavin is also suitable.

Skin pores in which such particles are lodged during use of the cream formulation of the present invention are gradually cleared of the particles as they dissolve fin the skin, releasing their helpful vitamins which are then absorbed by the skin.

As optional ingredients, oil-soluble vitamins and other materials which do not irritate the skin can be present in the formulation. Oil-soluble vitamins can be present because the skin has a natural oil content as well as water content.

The improved skin cream formulation of the present invention cleanses the skin and reduces its wrinkles and can be used by rubbing the formulation onto the skin in repeated applications until the desired effects are achieved, with excess amounts of the formulation being removed after each use. Improved skin tone, texture and health are obtained.

One manner of using the cream of the present invention is to employ the base for the cream by itself initially, by dipping the fingers into it and then touching the dipped fingers into a quantity of the particles of the formulation, thus forming the formulation by such combination. Rubbing of the skin with this combination substantially uniformly distributes the particles in the base as the rubbing proceeds. Other ways of using the present formulation will be obvious to one skilled in the art. The following specific examples illustrate certain features of the present invention.

EXAMPLE I

A skin cream formulation in accordance with the present invention is provided by substantially uniformly blending together the following ingredients:

a) 20% by weight of the formulation, of sodium chloride particles of an average particle diameter of a 1 millimeter; and, b) 80%, by weight of the formulation, of a base containing about equal proportions, by weight, of corn oil and petrolatum jelly.

When this formulation is rubbed on the skin in repeated applications and then removed with a soft cloth, the skin is softened, the outer keratinized layer of the skin is abraded and the skin's wrinkled areas are reduced in extent and depth, while the skin is cleansed of accumulated dirt, grime, etc. The sodium chloride particles gradually dissolve in contact with the skin, leaving the skin pores unclogged.

When parallel tests are carried out using particles of the materials described above, but with average particle sizes in the about 100–800 micron range, comparable results are obtained. The formulations in all instances are efficient, inexpensive and easy to prepare and use.

EXAMPLE II

A cream formulation in accordance with the present invention is prepared by substantially uniformly blending together the following ingredients:

a) about 15%. by weight of the formulation, of a mixture of about equal amounts of calcium pantothenate, calcium ascorbate and sodium para-aminobenzoate compressed into particles having an average Moh hardness of about 5–6 and an average particle diameter of about 700–800 microns; and, b) about 85%, by weight of the formulation, of a base formed of petrolatum jelly and vegetable oil, in a 3 to 1 weight ratio.

The resulting formulation has desirable skin-scouring, skin-enhancing and wrinkle-removing effects. The water-soluble vitamin-yielding salts used in the formulation are non-irritating to the skin and do not clog the pores thereof, but are gradually absorbed by the skin.

In a parallel test, sunflower seed oil is substituted for the petrolatum jelly to form a thin cream, providing comparable results to those set forth above. In a further test, the addition of small amounts of water-soluble and oil-soluble vitamins per se to the formulation do not interfere with the desirable effects of the formulation, but further enhance the nourishment added to the skin.

In a still further series of parallel tests, the vitamin-yielding salts are substituted for by:

1) as (ascorbic) acid granules in a 10%, by weight, concentration in a first test;

2) folic acid granules in a 5%, by weight, concentration in a second test;

3) thiamine hydrochloride granules in a 15%, by weight, concentration in a third test; and, 4) a mixture of 5%, by weight, of ascorbic acid granules and 15%, by weight, of thiamine hydrochloride granules in a fourth test.

These parallel tests provide comparable results to those set forth above.

What is claimed is:

1. In an improved skin cleansing and wrinkle-reducing cream, wherein the improvement comprises:
    a) an effective amount of a plurality of water-soluble, skin-abrading, non-irritating granules which are of at least one of a vitamin and a vitamin-yielding salt non-irritating to the skin; and
    b) an effective amount of an oleaginous creamy base non-irritating to the skin and in which said granules are substantially uniformly dispersed.

2. The improved skin cleansing cream of claim 1 wherein said base comprises at least one of an oil or petrolatum jelly.

3. The improved skin cleansing cream of claim 2 wherein said oil is an edible oil.

4. The improved skin cleansing cream of claim 1 wherein said granules include inorganic salt.

5. The improved skin cleansing cream of claim 4 wherein said granules include sodium chloride.

6. The improved skin cleansing cream of claim 1 wherein said vitamin comprises at least one of ascorbic acid, thiamine, riboflavin and folic acid.

7. The improved skin cleansing cream of claim 1 wherein said vitamin-yielding salt comprises at least one of calcium pantothenate, calcium ascorbate and sodium p-aminobenzoate.

8. The improved skin cleansing cream of claim 1 wherein said granules have an average diameter of about 105–700 microns, and sufficient hardness to abrade keratinized epidermis.

9. The improved skin cleansing cream of claim 1 wherein said cream has a wrinkle-removing effect upon repeated application to the skin with rubbing, and wherein said cream includes a minor proportion by weight of granulated particles of vitamin-yielding salt in a major proportion of an ointment comprising vegetable oil and petrolatum jelly.

* * * * *